United States Patent [19]

Glover et al.

[11] Patent Number: 5,435,996
[45] Date of Patent: Jul. 25, 1995

[54] MOISTURIZING COMPOSITIONS CONTAINING ORGANOSILICON COMPOUNDS

[75] Inventors: David A. Glover; Gary E. LeGrow; Linda M. Madore; Regina M. Malczweski, all of Midland, Mich.

[73] Assignee: Dow Corning Corporation, Midland, Mich.

[21] Appl. No.: 192,899

[22] Filed: Feb. 7, 1994

Related U.S. Application Data

[62] Division of Ser. No. 43,325, Apr. 6, 1993, Pat. No. 5,326,557.

[51] Int. Cl.$^6$ ............... A61K 7/48; A61K 31/765; C08K 5/54; C08L 83/06
[52] U.S. Cl. .................. 424/78.03; 424/70.11; 424/70.12; 424/70.19; 424/70.27; 424/70.28; 424/70.31; 424/401; 514/835; 514/837; 514/847; 514/858
[58] Field of Search ............... 424/70.11, 70.12, 70.19, 424/70.27, 70.28, 70.31, 78.03, 401; 514/847, 835, 858, 837; 252/312

[56] References Cited

U.S. PATENT DOCUMENTS

| | | | |
|---|---|---|---|
| 4,631,273 | 12/1986 | Blehm et al. | 252/312 |
| 4,902,499 | 2/1990 | Bolish, Jr. et al. | 424/70 |
| 5,108,738 | 5/1991 | Halloran et al. | 424/70 |
| 5,157,139 | 10/1992 | Legrow et al. | 556/470 |

*Primary Examiner*—Thurman K. Page
*Assistant Examiner*—Carlos Azpuru
*Attorney, Agent, or Firm*—James L. DeCesare

[57] ABSTRACT

Moisturizing compositions for application to human skin which contain oxyethylene functional organosilanes. When used in skin care applications, these compounds exhibit humectant properties. The oxyethylene functional organosilane is a compound having the formula $RSiR'_3$ in which R is the radical $-O(CH_2CH_2O)_xR''$; R' is an R group or an alkyl radical having one to six carbon atoms; R" is a radical such as hydrogen; an alkyl group of one to six carbon atoms; and an aryl group; and x is an integer having a value of six to thirty.

21 Claims, No Drawings

MOISTURIZING COMPOSITIONS CONTAINING ORGANOSILICON COMPOUNDS

This is a divisional of application Ser. No. 08/043,325 filed on Apr. 6, 1993 now U.S. Pat. No. 5,326,557.

BACKGROUND OF THE INVENTION

This invention is directed to moisturizing compositions for application to human skin which contain certain organosilicon compounds, more particularly oxyethylene functional organosilanes. When used in skin care applications, these compounds exhibit humectant properties.

Effective moisturizing amounts to the treatment of skin so that it can retain and absorb moisture. Typically, emollients such as oils and oleaginous materials, are applied to the skin for the purpose of forming an occlusive film on the skin, and hence emollients are known to relieve skin dryness by retarding the evaporation of moisture from the skin.

Humectants on the other hand, are capable of introducing moisture to the skin from the atmosphere in conditions of moderate or high humidity, and are capable of holding moisture in the skin, in order to maintain normal softness and pliability of the skin.

Organosilicon compounds containing oxyalkylene units are generally regarded as being useful for providing water solubility, surfactancy, and foaming, characteristics. Quite unexpectedly therefore, it has been discovered that certain oxyethylene functional organosilane compounds exhibit humectancy rather than occlusivity, and that these compounds provide humectant properties when applied to the skin.

Accordingly, these oxyethylene functional organosilane compounds can be utilized in a novel approach to skin moisturization, by including them as the skin conditioning agent in various skin care applications, including clear facial cleanser solutions, oil-in-water emulsion moisturizers, and aqueous skin care gels. Moisturization is optimized through the use of these compounds as an ingredient in various skin care formulations and in certain well defined proportions along with other combinations of ingredients.

SUMMARY OF THE INVENTION

The invention relates to skin moisturization, and to the provision of moisturization benefits to the skin through the use of the humectancy properties which have been found to be exhibited by certain oxyethylene functional organosilane compounds. These compounds possess the additional advantages in that they (i) are capable of detackifying common sticky skin care components, (ii) improve the aesthetic skin feel of formulations containing tacky ingredients, (iii) improve foam volumes in skin cleanser formulations, and (iv) provide a creamy more dense foam when employed in skin cleanser applications.

These and other objects, features, and advantages, of the herein defined present invention will become more apparent when considered in light of the following detailed description thereof.

DETAILED DESCRIPTION OF THE INVENTION

The skin conditioning agent employed in accordance with the present invention is an oxyethylene functional organosilane compound having the formula $RSiR'_3$ in which R is the radical $-O(CH_2CH_2O)_xR''$; $R'$ is an R group or an alkyl radical having one to six carbon atoms; $R''$ is a radical selected from the group consisting of hydrogen; an alkyl group of one to six carbon atoms such as methyl, ethyl, propyl, and butyl; and an aryl group such as phenyl and benzyl; and x is an integer having a value of six to thirty. Preferably, x has a value of twelve to twenty.

These oxyethylene functional organosilanes may be prepared for example by methods involving the reaction of a silazane with an organic alcohol in the presence of an inorganic catalyst. Such methods of preparation are described in detail in U.S. Pat. No. 5,157,139 issued Oct. 20, 1992, which patent is incorporated herein by reference.

Skin care compositions in accordance with the concepts of the present invention are illustrated in the following examples. The particular oxyethylene functional organosilane which was employed in these examples to prepare the various skin care compositions had the formula $(CH_3)_2Si[O(CH_2CH_2O)_{16}H]_2$.

EXAMPLE I

A clear facial cleanser was prepared by combining the various ingredients of Parts A-D which are set forth below in Table I in the proportions shown in the table. The procedure to prepare the clear facial cleanser was begun by heating water to fifty degrees Centigrade. The other ingredients of Part A were added to the heated water in order, and mixed until homogeneous. The pH of the mixture was adjusted to about seven with citric acid, and mixing was continued. The oxyethylene functional organosilane was heated to fifty degrees Centigrade and added to the mixture, and mixing was continued. The preservative was added, and the mixture was cooled to room temperature under slow mixing. Stability testing of the resulting clear facial cleanser solution revealed that the solution was stable for at least four months at room temperature, four months at forty degrees Centigrade, and following three freeze/thaw cycles.

TABLE I

| Part | Ingredient | Percent by Weight |
|---|---|---|
| A | Deionized Water | 60.0 |
| A | Disodium Cocoamphodiacetate MIRANOL ® C2M Conc. NP (Amphoteric surfactant) | 12.0 |
| A | Sodium Lauryl Sarcosinate HAMPOSYL L-30 (Anionic Surfactant) | 10.0 |
| A | Cocamidopropylbetaine MIRATAINE ® CB (Amphoteric Surfactant) | 8.0 |
| A | Lauramide DEA MONAMID 1089 (Nonionic Surfactant) | 4.0 |
| B | Citric Acid (50 percent) | 0.5 |
| C | Oxyethylene Functional Silane | 5.0 |
| D | Preservative: Mixture of Propylene Glycol, Methylparaben, Propylparaben, and Diazolidinyl Urea (GERMABEN ® II) | 0.5 |

In Table I, the amphoteric surfactant MIRANOL ® C2M Conc. NP is a trademark and a product of Rhone-Poulenc Incorporated, Cranberry, N.J. The anionic surfactant HAMPOSYL L-30 is a product of W. R. Grace & Company, Lexington, Mass. The amphoteric surfactant MIRATAINE ® CB is a trademark and a product of Rhone-Poulenc Incorporated, Cranberry, N.J. The nonionic surfactant MONAMID 1089 is a product of Mona Industries Incorporated, Paterson, N.J. The preservative GERMABEN® II is a trademark and a product of Sutton Laboratories, Chatham, N.J.

EXAMPLE II

A moisturizer in the form of an oil-in water emulsion was prepared by combining the various ingredients of Parts A-E which are set forth below in Table II in the proportions shown in the table. The procedure to prepare the moisturizer was begun by dispersing the thickener of Part A in deionized water until uniform, and heating the mixture to seventy degrees Centigrade. The thickener employed in Part A was a polyacrylate sold under the trademark CARBOPOL® 940 by B. F. Goodrich Company, Cleveland, Ohio. The ingredients of Part B were mixed together and heated to seventy degrees Centigrade. Part B was added to Part A and mixed until homogeneous. Triethanolamine was added to neutralize the emulsion, and the emulsion was allowed to begin cooling. The oxyethylene functional organosilane was heated to fifty degrees Centigrade, added slowly to the mixture, and mixing was continued until uniform. The preservative and fragrance were added, and the emulsion was mixed and cooled to room temperature.

TABLE II

| Part | Ingredient | Percent by Weight |
|---|---|---|
| A | Deionized Water | 77.19 |
| A | CARBOPOL® 940 (Thickener) | 0.3 |
| B | Stearic Acid | 3.0 |
| B | Glyceryl Stearate & PEG 100 Stearate ARLACEL 165 (Nonionic Surfactant) | 2.0 |
| B | Stearyl Alcohol (Thickener) | 1.0 |
| B | Mineral Oil (Emollient) | 5.0 |
| C | Triethanolamine | 0.5 |
| D | Oxyethylene Functional Silane | 10.0 |
| D | Preservative: Mixture of Propylene Glycol, Methylparaben, Propylparaben, and Diazolidinyl Urea (GERMABEN® II) | 1.0 |
| E | Fragrance | 0.01 |

In Table II, the nonionic surfactant ARLACEL 165 is a product of ICI Americas Incorporated, Wilmington, Del. Triethanolamine stearate, an anionic surfactant, was formed "in situ" from stearic acid and triethanolamine which were present in the formulation.

EXAMPLE III

A skin treating composition in the form of an aqueous gel was prepared by combining the various ingredients of Parts A-D which are set forth below in Table III in the proportions shown in the table. The procedure to prepare the aqueous gel was begun by dispersing the thickener CARBOPOL® 940 of Part A in deionized water until uniform, and neutralizing the mixture with triethanolamine. The ingredients of Part B were added to Part A in order and mixed until uniform. The oxyethylene functional organosilane was heated to fifty degrees Centigrade, added slowly to the mixture, and mixing was continued until uniform. The preservative and color were added, and mixing was continued until homogeneous.

TABLE III

| Part | Ingredient | Percent by Weight |
|---|---|---|
| A | Deionized Water | 91.58 |
| A | CARBOPOL® 940 (Thickener) | 0.3 |
| A | Triethanolamine | 0.3 |
| B | Sorbitol (Humectant) | 2.0 |
| B | Hydrolyzed Mucopolysaccharides (Humectant) | 1.0 |
| B | Menthol (Fragrance) | 0.01 |
| B | Panthenol (Humectant) | 0.1 |
| B | PEG 75 Lanolin (Lubricant) | 1.5 |
| C | Oxyethylene Functional Silane | 3.0 |
| D | DMDM Hydantoin GLYDANT® (Preservative) | 0.2 |
| D | FD & C Blue No. 1 (1.0 percent) | 0.01 |

In Table III, the preservative GLYDANT® is a trademark and a product of Lonza Incorporated, Fair Lawn, N.J.

EXAMPLE IV

Conductance and Capacitance measurements were used to determine the humectancy properties of the oxyethylene functional organosilane material. A Skicon-100 Hydrometer was used to measure the conductance of skin surface. Since water is a good conductor of electrical current, when more water is present in the stratum corneum, the conductance measurements are higher. Measurements via a Corneometer instrument register the electrical capacitance of the skin surface. Like the conductance measurements, higher readings in capacitance mean more moisture is present. In Tables IV and V shown below, the conductance and capacitance measurements "in vivo" on skin show that the oxyethylene functional organosilanes of the present invention possess humectant properties of moisture binding above untreated skin capable of lasting through a minimum period of six hours. Glycerine was used as a positive control. In the tables, zero is normalized data for untreated skin. The Glycerine and silane values are differences relative to untreated skin.

TABLE IV

| CORNEOMETER MEASUREMENTS | | | |
|---|---|---|---|
| Hours Post-Dose | Skin | Glycerin | Silane |
| 0 | 0 | 23.4 | 11.6 |
| 1 | 0 | 12.6 | 15.4 |
| 2 | 0 | 8.6 | 10.1 |
| 3 | 0 | 9.1 | 8.1 |
| 4 | 0 | 9.4 | 8.9 |
| 5 | 0 | 9.3 | 8.5 |
| 6 | 0 | 8.0 | 6.8 |

TABLE V

| CONDUCTANCE MEASUREMENTS | | | |
|---|---|---|---|
| Hours Post-Dose | Skin | Glycerin | Silane |
| 0 | 0 | 682.1 | 126.3 |
| 1 | 0 | 413.3 | 124.4 |
| 2 | 0 | 379.2 | 171.5 |
| 3 | 0 | 370.6 | 116.7 |
| 4 | 0 | 354.4 | 126.3 |
| 5 | 0 | 313.0 | 87.3 |

TABLE V-continued

| CONDUCTANCE MEASUREMENTS | | | |
|---|---|---|---|
| Hours Post-Dose | Skin | Glycerin | Silane |
| 6 | 0 | 288.5 | 75.8 |

In general, skill care compositions in accordance with the present invention may be prepared by combining the ingredients in amounts varying from 0.1 to 20.0 percent by weight of the oxyethylene functional organosilane; 20.0 to 95.0 percent by weight of water; less than one percent by weight of one or more preservatives; 3.0 to 50.0 percent by weight of one or more surfactants; 0.05 to 5.0 percent by weight of one or more thickening agents; 0.05 to 1.0 percent by weight of a fragrance; and zero to twenty percent by weight of one or more emollients or humectants.

Skin care compositions in the form of clear facial cleanser solutions as embodied in Example I, may be prepared by combining the ingredients in amounts varying from 3.0 to 10.0 percent by weight of the oxyethylene functional organosilane; 40.0 to 60.0 percent by weight of water; 0.2 to 0.5 percent by weight of one or more preservatives; 10.0 to 30.0 percent by weight of one or more surfactants; 1.0 to 2.0 percent by weight of one or more thickening agents; 0.01 to 0.25 percent by weight of a fragrance; and 0.5 to 3.0 percent by weight of one or more emollients or humectants.

Skin care compositions in the form of an oil-in-water emulsion moisturizer as embodied in Example II, may be prepared by combining the ingredients in amounts varying from 3.0 to 10.0 percent by weight of the oxyethylene functional organosilane; 40.0 to 80.0 percent by weight of water; 0.2 to 0.5 percent by weight of one or more preservatives; 2.0 to 10.0 percent by weight of one or more surfactants; 0.1 to 3.0 percent by weight of one or more thickening agents; 0.01 to 1.0 percent by weight of a fragrance; and 0.5 to 10.0 percent by weight of one or more emollients or humectants.

Skin care compositions in the form of an aqueous gel as embodied in Example III, may be prepared by combining the ingredients in amounts varying from 0.5 to 5.0 percent by weight of the oxyethylene functional organosilane; 70.0 to 95.0 percent by weight of water; 0.2 to 0.5 percent by weight of one or more preservatives; 0.5 to 5.0 percent by weight of one or more surfactants; 0.1 to 1.0 percent by weight of one or more thickening agents; 0.01 to 0.5 percent by weight of a fragrance; and 0.5 to 10.0 percent by weight of one or more emollients or humectants.

It can be seen from the foregoing description that various ingredients are used to formulate products in accordance with the present invention including surfactants, pH modifiers, preservatives, thickening agents, emollient oils, fragrances, neutralizing agents, humectants, and colorants.

In addition, it may be desirable to include other materials such as waxes; sunscreen agents; vitamins such as Vitamin A, Vitamin B, Vitamin D, Vitamin E, ascorbic acid, and biotin; hormones; amino acids; antioxidants such as propyl, octyl, and dodecyl esters of gallic acid, butylated hydroxytoluene, butylated hydroxyanisole, and natural mixed tocopherols; opacifiers such as titanium dioxide and fatty alcohols; and solvents such as ethanol and isopropanol.

Waxes which may be employed include carnauba, beeswax, ceresin, paraffin, candelilla, bayberry, montan, spermaceti, castor wax, ozokerite, microcrystalline waxes, and Fisher-Tropsch waxes. Colorants include any of tile United States Government Food & Drug Administration (FDA) certified organic dyes and lakes.

Preservatives which may be used are methyl paraben, propyl paraben, butyl paraben, diazolidinyl urea, imidazolidinyl urea, and mixtures thereof. Where an antimicrobial is required, materials such as Triclosan, Quaternium-15, chloroxylenol, and cetyl trimethyl ammonium bromide, may be employed.

It is preferred to utilize an acid to adjust the pH to within the range of five to nine, preferably six to eight. Any water soluble acid such as a carboxylic acid or a mineral acid can be employed. Acids which may be used include mineral acids such as hydrochloric, sulfuric, and phosphoric acid; monocarboxylic acids such as acetic, lactic, and propionic acid; and polycarboxylic acids such as succinic, adipic, and citric acid.

Suitable neutralizing agents include sodium hydroxide, potassium hydroxide, ammonium hydroxide, monoethanolamine, diethanolamine, and triethanolamine. Among the numerous humectants which may be employed are sorbitol, glycerine, alkoxylated glucose, hexanetriol, panthenol, hydrolyzed mucopolysaccharides, and mixtures thereof.

Emollient oils which can be employed in the present invention include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil; fatty acid esters such as isopropyl myristate, isopropyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, isostearyl, oleyl, ricinoleyl, erucyl, and 2-octyl dodecanol, alcohol; lanolin and its derivatives such as lanolin, lanolin oil, lanolin wax, lanolin alcohols, lanolin fatty acids, isopropyl lanolate, and ethoxylated lanolin; and silicones such as non-volatile siloxane fluids and volatile siloxane fluids.

Sunscreen agents may be included in some instances, and can be used in amounts which are within the restricted limits or less as established by the United States Government Food & Drug Administration (FDA). Representative sunscreen agents or mixtures of such agents which may be used in the preparation of the compositions of the present invention include 4-aminobenzoic acid; homomethyl salicylate; 2-hydroxy-4-methoxy benzophenone; 2-phenylbenzimidazol-5-sulfonic acid; 4-dimethylamino benzoic acid 2-ethylhexyl ester; 4-methoxy cinnamic acid isoamyl ester; 4-methoxy cinnamic acid 2-ethylhexyl ester; 3-(4'-methyl) benzylidine-bornane-2-one; 1-(4'-isopropylphenyl)-3-phenyl-1-propane-1,3-dione; and 1-(4'-t-butylphenyl)-3-(4-methoxyphenyl)propane-1,3-dione.

Fragrances which may be used include natural products such as ambergris, benzoin, civet, clove, leaf oil, jasmine, mate', mimosa, musk, myrrh, orris, sandalwood oil and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Non-volatile silicone fluids which may be used in the preparation of the compositions of the present invention are organic polysiloxanes having a viscosity in the range of about 5 to as high as several million centistokes, preferably about 100 to about 10,000 centistokes. A mixture of polysiloxanes having relatively higher and relatively lower viscosities can employed. Such polysiloxanes have the repeating unit

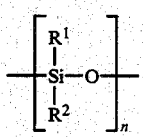

wherein n is an integer having a value greater than 1; $R^1$ and $R^2$ are alkyl radicals of one to seven carbon atoms, or a phenyl group; and $R^1$ and $R^2$ may be the same or different. Illustrative polysiloxanes are polydimethylsiloxane, polydiethylsiloxane, polymethylethylsiloxane, polymethylphenylsiloxane, polydiphenylsiloxanes, and copolymers of two or more of the foregoing siloxanes.

Where it is desirable to include a volatile silicone fluid in the compositions of the present invention, suitable volatile silicones are low viscosity methylsilicones. The volatile low viscosity methylsilicone fluid corresponds to the average unit formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{\frac{1}{2}}$, $(CH_3)_2SiO_{2/2}$, $(CH_3)SiO_{3/2}$, and $SiO_{4/2}$. These units are present in molar amounts such that there is provided an average of from about two to three methyl groups per silicon atom in the methylsilicone fluid, whereby the methylsilicone fluid has a viscosity of less than about one hundred centistokes measured at twenty-five degrees Centigrade.

The volatile low viscosity methylsilicone fluid contains dimethylsiloxane units and optionally trimethylsiloxane units. Preferably, the methylsilicone fluid has a viscosity of less than about ten centistokes. Representative compounds are cyclopolysiloxane compounds of the general formula $[(CH_3)_2SiO]_x$, and linear siloxane compounds of the general formula $(CH_3)_3SiO[(CH_3)_2SiO]_ySi(CH_3)_3$, in which x is an integer having a value of from three to ten, and y is an integer having a value of from zero to about four.

The volatile low viscosity methylsilicones have boiling points generally less than about two hundred-fifty degrees Centigrade, and possess viscosities preferably generally less than about ten centistokes measured at twenty-five degrees Centigrade. Most preferably, the viscosity is 0.65 to 5.0 centistokes. The cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in accordance with the present invention are hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; and decamethylcyclopentasiloxane which has a boiling point of 205 degrees Centigrade and the formula $[(Me_2)SiO]_5$.

These methylsilicone fluids may be used alone, or as mixtures in combinations of two or more. Mixtures of the methylsilicone fluids will result in a volatile material having an evaporating behavior different from any one of the individual methylsilicone fluids. The methylsilicone fluids and methods for their preparation are known in the art, and such fluids are commercially available.

In some instances, it may be desirable to replace one or more of the methyl groups in the methylsilicone fluid with other groups. Thus, there may be substituted groups such as alkyl radicals having two to twelve carbon atoms; aryl radicals having six to ten carbon atoms; amine groups; vinyl; hydroxyl; haloalkyl groups; aralkyl groups; and acrylate groups, for example.

The compositions of this invention as noted above may contain a surfactant such as an anionic and amphoteric surfactant. Suitable anionic surfactants include sulfonated and sulfated alkyl, aralkyl and alkaryl anionic surfactants; alkyl succinates; alkyl sulfosuccinates and N-alkyl sarcosinates. Representative surfactants are the sodium, magnesium, ammonium, and the mono-, di- and triethanolamine salts of alkyl and aralkyl sulfates as well as the salts of alkaryl sulfonates. The alkyl groups of the surfactants generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic surfactants include, among others, sodium lauryl sulfate, sodium lauryl ether sulfate, ammonium lauryl sulfate, triethanolamine lauryl sulfate, sodium C14-16 olefin sulfonate, ammonium pareth-25 sulfate (ammonium salt of a sulfated polyethylene glycol ether of a mixture of synthetic C12-15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate.

Surfactants generally classified as amphoteric or ampholytic include cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric surfactants include the quaternary cycloimidates, betaines, and sultaines.

The betaines may have the structure:

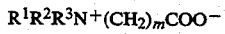

wherein $R^1$ is an alkyl group having about 12 to 18 carbon atoms or a mixture thereof $R^2$ and $R^3$ are independently lower alkyl groups having 1 to 3 carbon atoms, and m is an integer from 1 to 4. Specific betaines are alpha-(tetradecyldimethylammonio)acetate, beta-(hexadecyldiethylammonio)propionate, and gamma-(dodecyldimethylammonio)butyrate.

The sultaines may have the structure:

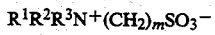

wherein $R^1$, $R^2$, $R^3$, and m are defined as above. Specific useful sultaines are 3-(dodecyldimethylammonio)-propane-1-sulfonate, and 3-(tetradecyldimethylammonio)ethane-1-sulfonate.

The compositions of this invention may contain a nonionic surfactant which is a fatty acid alkanolamide or amine oxide surfactant. The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide.

The amine oxides are known nonionic surfactants obtained by oxidizing a tertiary amine to form the amine oxide. They are sometimes referred to as polar nonionic surfactants. Amine oxide surfactants include, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxy-propylamine oxide. The hydrophobic portion of the amine oxide surfactants is generally provided by a fatty hydrocarbon chain containing from 10 to 21 carbon atoms. Representative surfactants include lauric acid diethanolamide, N-lauryl dimethylamine oxide, coconut acid diethanolamide, myristic acid diethanolamide, and oleic acid diethanolamide.

Additional categories of surfactants may be included such as cationic and zwitterionic surfactants, and representative compounds are set forth in detail in U.S. Pat. No. 4,902,499, issued Feb. 20, 1990.

Suitable thickeners which may be employed are sodium alginate, gum arabic, polyacrylates, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as sodium or ammonium chloride, saccharides such as fructose and glucose, and derivatives of saccharides such as PEG-120 methyl glucose dioleate.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. A method of moisturizing skin comprising applying to the skin a skin conditioning composition which comprises 0.1 to 20.0 percent by weight based on the total weight of the skin conditioning composition of a skin conditioning agent which is an oxyethylene functional organosilane compound having the formula $RSiR'_3$ in which R is the radical $-O(CH_2CH_2O)_xR''$; $R'$ is an R group or an alkyl radical having one to six carbon atoms; $R''$ is a radical selected from the group consisting of hydrogen; an alkyl group of one to six carbon atoms; and an aryl group; and x is an integer having a value of six to thirty.

2. A method according to claim 1 in which the value of the integer x is twelve to twenty.

3. A method according to claim 2 in which the oxyethylene functional organosilane compound has the formula $(CH_3)_2Si[O(CH_2CH_2O)_{16}H]_2$.

4. A method of moisturizing skin comprising applying to the skin a skin care composition which comprises 3.0 to 50.0 percent by weight of at least one surfactant selected from the group consisting of anionic, nonionic, and amphoteric, emulsifying agents; 0.1 to 20.0 percent by weight of a skin conditioning agent; 0.05 to 5.0 percent by weight of a thickening agent; 1,0 to 20.0 percent by weight of an emollient or humectant; and the balance being water; the skin conditioning agent being an oxyethylene functional organosilane compound having the formula $RSiR'_3$ in which R is the radical $-O(CH_2CH_2O)_xR''$; $R'$ is an R group or an alkyl radical having one to six carbon atoms; $R''$ is a radical selected from the group consisting of hydrogen; an alkyl group of one to six carbon atoms; and an aryl group; and x is an integer having a value of six to thirty.

5. A method according to claim 4 in which the surfactant is a mixture of an amphoteric emulsifying agent and a nonionic emulsifying agent.

6. A method according to claim 4 in which the value of the integer x is twelve to twenty.

7. A method according to claim 4 in which the oxyethylene functional organosilane compound has the formula $(CH_3)_2Si[O(CH_2CH_2O)_{16}H]_2$.

8. A method of moisturizing skin comprising applying to the skin a skin care facial cleanser composition in the form of a solution which comprises 10.0 to 30.0 percent by weight of at least one surfactant selected from the group consisting of anionic, nonionic, and amphoteric, emulsifying agents; 3.0 to 10.0 percent by weight of a skin conditioning agent; and the balance being water; the skin conditioning agent being an oxyethylene functional organosilane compound having the formula $RSiR'_3$ in which R is the radical $-O(CH_2C-H_2O)_xR''$; $R'$ is an R group or an alkyl radical having one to six carbon atoms; $R''$ is a radical selected from the group consisting of hydrogen; an alkyl group of one to six carbon atoms; and an aryl group; and x is an integer having a value of six to thirty.

9. A method according to claim 8 in which the surfactant is a mixture of an amphoteric emulsifying agent and a nonionic emulsifying agent.

10. A method according to claim 8 in which the value of the integer x is twelve to twenty.

11. A method according to claim 8 in which the oxyethylene functional organosilane compound has the formula $(CH_3)_2Si[O(CH_2CH_2O)_{16}H]_2$.

12. A method of moisturizing skin comprising applying to the skin a skin care moisturizing composition in the form of an oil-in-water emulsion which comprises 2.0 to 10.0 percent by weight of at least one surfactant selected from the group consisting of anionic, nonionic, and amphoteric, emulsifying agents; 3.0 to 10.0 percent by weight of a skin conditioning agent; 0.5 to 10.0 percent by weight of an emollient oil; and the balance being water; the skin conditioning agent being an oxyethylene functional organosilane compound having the formula $RSiR'_3$ in which R is the radical $-O(CH_2CH_2O)_xR''$; R' is an R group or an alkyl radical having one to six carbon atoms; R'' is a radical selected from the group consisting of hydrogen; an alkyl group of one to six carbon atoms; and an aryl group; and x is an integer having a value of six to thirty.

13. A method according to claim 12 in which the surfactant is a mixture of an anionic emulsifying agent and a nonionic emulsifying agent, the anionic emulsifying being formed in situ.

14. A method according to claim 12 in which the value of the integer x is twelve to twenty.

15. A method according to claim 12 in which the oxyethylene functional organosilane compound has the formula $(CH_3)_2Si[O(CH_2CH_2O)_{16}H]_2$.

16. A method according to claim 12 further including 0.1 to 3.0 percent by weight of a thickening agent.

17. A method of moisturizing skin comprising applying to the skin an aqueous skin conditioning gel composition which comprises 0.5 to 5.0 percent by weight of a skin conditioning agent; 0.1 to 1.0 percent by weight of a thickening agent; 0.5 to 10.0 percent by weight of a humectant; and the balance being water; the skin conditioning agent being an oxyethylene functional organosilane compound having the formula $RSiR'_3$ in which R is the radical $-O(CH_2CH_2O)_xR''$; R' is an R group or an alkyl radical having one to six carbon atoms; R'' is a radical selected from the group consisting of hydrogen; an alkyl group of one to six carbon atoms; and an aryl group; and x is an integer having a value of six to thirty.

18. A method according to claim 17 in which the value of the integer x is twelve to twenty.

19. A method according to claim 17 in which the oxyethylene functional organosilane compound has the formula $(CH_3)_2Si[O(CH_2CH_2O)_{16}H]_2$.

20. A method according to claim 17 in which the humectant is mixture containing sorbitol, panthenol, and hydrolyzed mucopolysaccharides.

21. A method according to claim 20 further including a lanolin derivative as a lubricant.

* * * * *